United States Patent [19]

Vancells

[11] Patent Number: 5,245,033
[45] Date of Patent: Sep. 14, 1993

[54] PROCESS FOR PRODUCING CYANURIC ACID

[75] Inventor: Luis E. Vancells, Barcelona, Spain

[73] Assignee: Patentes Y Novedades, S.L., Barcelona, Spain

[21] Appl. No.: 917,967

[22] Filed: Jul. 24, 1992

[30] Foreign Application Priority Data

Aug. 21, 1991 [ES] Spain .................................. 9101916

[51] Int. Cl.$^5$ ........................................... C07D 251/32
[52] U.S. Cl. .................................................. 544/192
[58] Field of Search ......................................... 544/192

[56] References Cited

FOREIGN PATENT DOCUMENTS 1183672 7/1959 France .
43289 2/0563 Luxembourg .

Primary Examiner—John M. Ford
Attorney, Agent, or Firm—Staas & Halsey

[57] ABSTRACT

The plant is provided with a first rotary reactor where the balls of urea cyanurate are formed and a second reactor where the pyrolysis takes place. The first reactor is provided with an internal helical fin and the second reactor is also rotary. At the exit thereof there is a communication tube placing it in communication with a solids separator vessel which receives an aqueous solution capable of reaching a working level, below which there is the access port of the tube to the vessel. The vessel is provided with a lower drain valve and an upper gas exhaust tube.

1 Claim, 2 Drawing Sheets

PROCESS FOR PRODUCING CYANURIC ACID

BACKGROUND OF THE INVENTION

1. Field of the Invention

The invention relates to a plant for producing cyanuric acid by pyrolysis of urea, comprising a first rotary cylindrical reactor in which the urea cyanurate balls are formed and a second reactor where said pyrolysis takes place.

The invention also relates to a process for the preparation of cyanuric acid, comprising a first step of preparation of urea cyanurate by reaction, in a first rotary reactor, of urea with recirculated cyanuric acid and a second step of pyrolysing the urea cyanurate in a second reactor.

2. Description of the Prior Art

Cyanuric acid is prepared on an industrial scale from urea by pyrolysis thereof, with or without a solvent, as per the following reaction:

$$3\ H_2NCONH_2 \rightarrow C_3H_3N_3O_3 + 3\ NH_3$$

The processes using a solvent have the common drawback of the recovery thereof and also the subsequent environmental problem. This means that they are not economically advantageous. The dry methods are preferable, although here the problems arise from the soiling of the reactors during pyrolysis. The soiling is of such a degree that, unless precautions are taken, it reaches the extreme of invalidating the process. Several processes have been devised to solve this problem. Some use an acid catalyst and the majority try to increase the heat exchange in some way, either by mixing the urea with a molten metal, by fluidisation or, more frequently, by using a tubular reactor.

These reactors must be provided with a blade system scraping the wall thereof to remove the furring which inevitably forms. Such reactors are described in U.S. Pat. No. 2,943,088, FR 1,183,672, ES 520,763 and U.S. Pat. No. 4,474,957. Nevertheless, these reactors, although to a lesser extent, continue to give soiling problems obliging the plants to be shut down periodically for cleaning. The process is improved if the urea cyanurate is prepared prior to pyrolysis by reaction of the cyanuric acid on the molten urea, which is then subjected to the pyrolysis as such. This process may be carried out in two different reactors (U.S. Pat. No. 3,318,887) or in a single one having different temperature zones (ES 540,265), or in such a way that the molten urea is distributed through different inlets in the furnace (U.S. Pat. No. 4,474,957). Of these options, the last two require much more complex control instrumentation and a larger furnace also, leading to high investment and maintenance costs. The first option is preferable, since although it requires two reactors, the first one is very simple to construct and the second one carries out the pyrolysis integrally under particular fixed conditions, whereby the control of the operative conditions is simplified.

U.S. Pat. No. 3,318,887 gives as an example of a reactor in which the urea cyanurate may be formed a rotary drum provided with fixed internal blades. The patent likewise teaches that the working temperature in the first reactor should range from 125° to 160° C. A drawback of this process is the formation of lumps, since the balls are scarcely well formed or, if they are, they break on colliding against the blades. A time also comes with this plant when it must be shut down for cleaning purposes.

Another drawback in the manufacture of cyanuric acid is to be found in the scrubbing column for the gases exhausting from the reactor. Apart from the ammonia formed in the reaction, these gases also entrain sublimated urea, finely divided cyanuric acid and a number of products derived from the reaction, such as cyanic acid, ammonium cyanate and carbamates. These products accompanying the NH3 finally block the scrubbing column, in spite of the improvement introduced in U.S. Pat. No. 2,943,088, consisting of scrubbing the gases with a current of hot urea, and this means that the plant must be shut down for cleaning.

SUMMARY OF THE INVENTION

It is an object of the invention to overcome the above mentioned drawbacks. This object is achieved by a plant of the type first mentioned above which is characterized in that said first reactor is provided with a helical fin extending inwardly from the internal cylindrical surface thereof and in that said second reactor is also rotary, and at the exit thereof there is at least one communication tube placing the second reactor in communication with a solids separator vessel, which is adapted to receive an aqueous solution which may reach a working level below which there is the access port of said tube to said vessel; said separator being provided with a lower drain valve and with an upper gas exhaust tube.

The said separator vessel is fundamental to avoid the frequent blockages otherwise affecting the ammonia absorption column.

The process which is also an object of the present invention is characterized in turn in that said first reactor, on the one hand, is provided with a helical fin extending inwardly from the internal cylindrical surface thereof and, on the other hand, is heated to a temperature ranging from 180° to 350° C., there being obtained balls of urea cyanurate, the dryness of which facilitates the transportation thereof, at the same time as it avoids the agglomeration thereof and subsequent adherence to the walls of the second reactor, while said second reactor is rotary and is in communication, by means of a communication tube, with a solids separator vessel in which there is to be found an aqueous solution, setting a working level under which there is the access port of said tube to said vessel, said aqueous solution receiving the solid products formed in the pyrolysis and being periodically renewed by removal of the suspension formed and supply of fresh aqueous solution.

BRIEF DESCRIPTION OF THE DRAWINGS

Further advantages and features of the invention will be appreciated from the following description in which there is described a preferred embodiment of the invention without any limiting nature and with reference to the accompanying drawings. The drawings show.

DETAILED DESCRIPTION OF THE INVENTION

Figure 1:
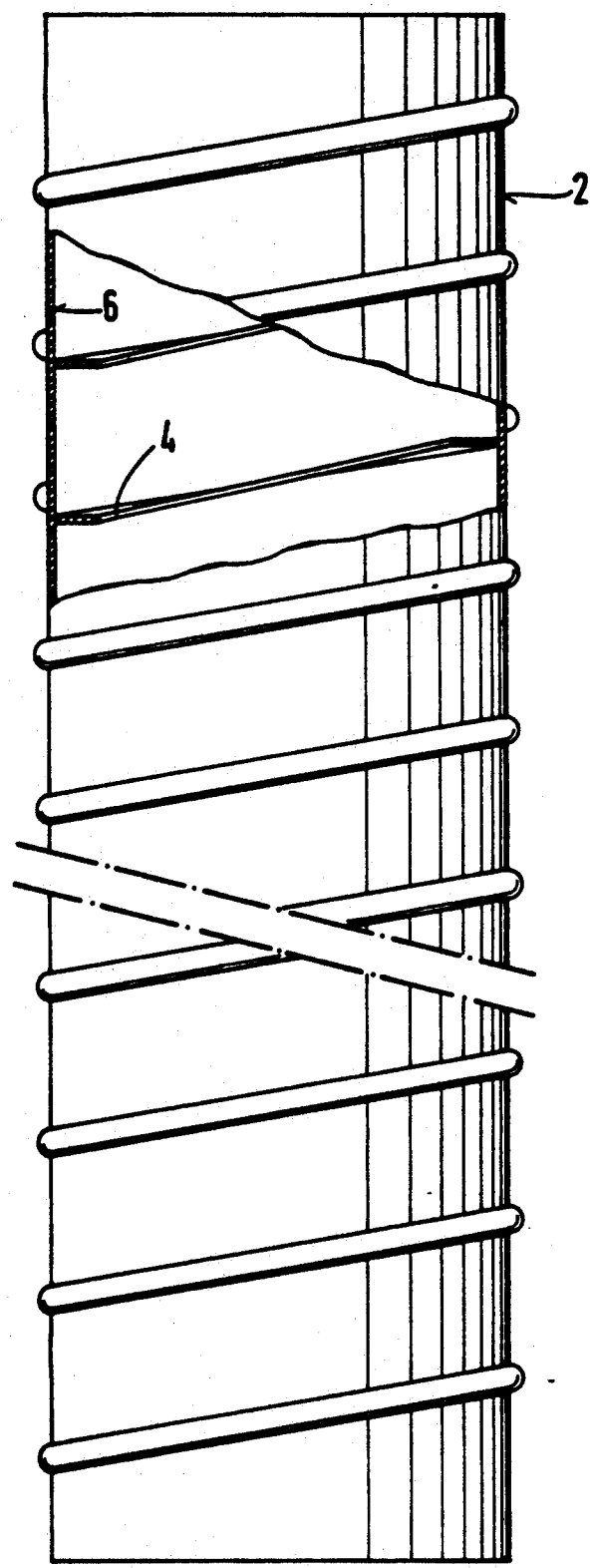
FIG. 1, a schematic, partly cross section view of the first reactor of the plant of the invention.
Figure 2:
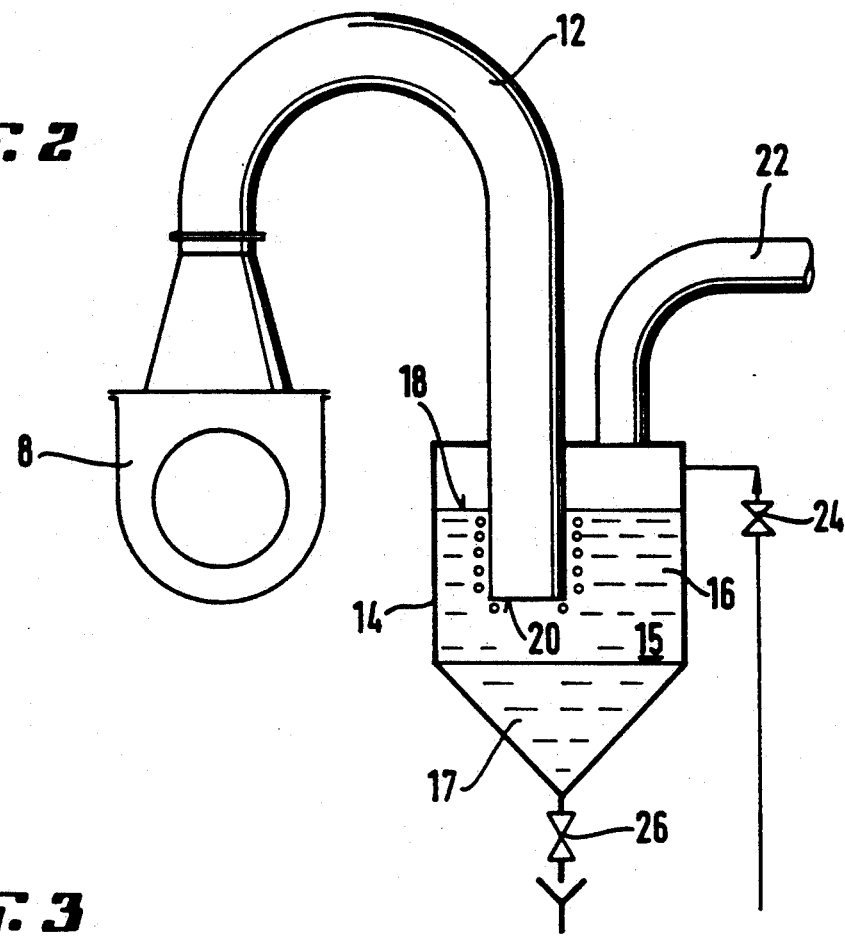
FIG. 2, a schematic elevation view of the second reactor and of the separator vessel.
Figure 3:
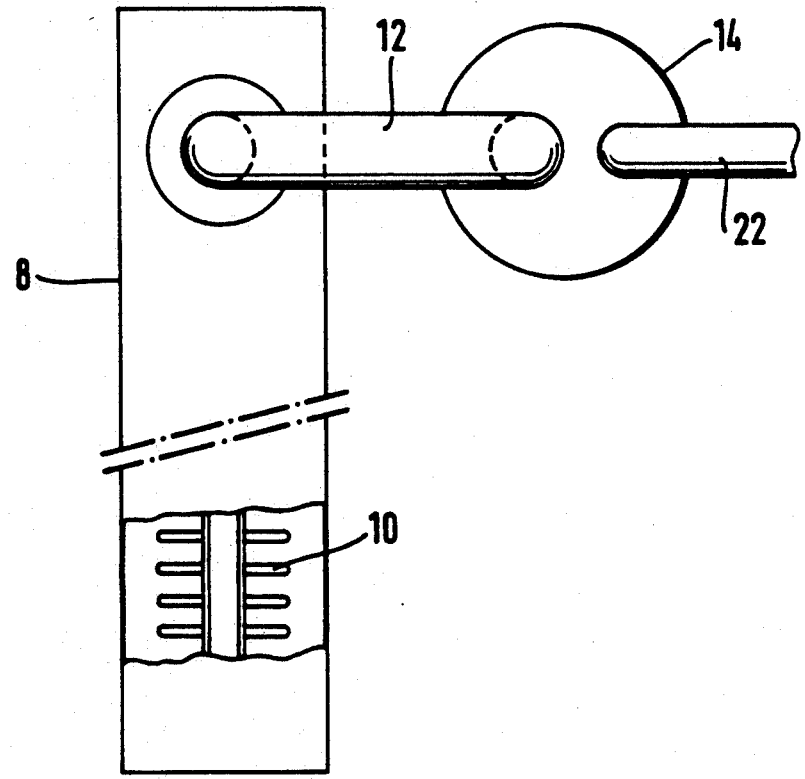
FIG. 3, a schematic plan view of the second reactor and of the separator vessel.

The first reactor 2 is a cylindrical tube, rotating, preferably at a speed of from 4 to 40 r.p.m., and is provided with a helical fin 4 extending inwardly from the inner surface 6 of the reactor 2. The fin 4 is preferably welded and leaves an inner empty space for the passage of the product.

The length of the reactor ranges preferably from 6 to 12 m, the diameter being of the order of 0.5 to 1 m. In turn, the radial dimension of the fin 4 extends over from 10 to 30% of the inner diameter dimension of the reactor and, therefore, the preferred dimensions are from 0.05 to 0.3 m, while the gap between the consecutive coils is from 0.15 to 0.4 m. A thermal fluid is caused to flow through the jacket heating the reactor to a temperature ranging from 180° to 350° C.

The use of said helical fin instead of the conventional fins, as well as the working conditions referred to above, particularly a product temperature at the exit of the reactor 2 of above 180° C., allows urea cyanurate balls to be obtained which do not stick and which may be fed into the second reactor 8 with great ease, since the dryness thereof makes them easily transportable without forming lumps or sticking to the walls of the second reactor 8.

It is desirable periodically to inject (e.g. every 24 hours) a small amount of water or steam, whereby the furring softens and is released from the wall. In this way the heat exchange surface is kept clean, without having to shut the plant down.

The second reactor 8 is also rotary preferably at a speed of 5 to 25 r.p.m. For the heating thereof, it is provided with discs 10 through which thermal fluid flows, it being desirable for it to reach a temperature ranging from 200° to 350° C. The preferred dimensions of the reactor 8 are from 5 to 10 m long and from 0.5 to 1 m diameter.

According to the invention, at the exit of the second reactor there is at least one communication tube 12, in siphon form, placing it in communication with a solids separator vessel 14, the height of which ranges preferably from 0.5 to 2 m and which has an upper cylindrical portion 16 having a diameter on the order of 0.5 to 1 m, followed by a lower conical portion 17. An aqueous solution 15 (preferably formed by water, an alkali hydroxide, preferably sodium hydroxide solution, or a urea solution), determining a level 18, is poured into the vessel 14, so that the access port 20 of the tube 12 to the vessel 14 is from 0.05 to 0.5 m below said level 18.

The separator vessel 14 is provided with a gas exhaust tube 22 and the aqueous solution 15 is renewed by the supply of fresh solution through the valve 24. Preferably the solution temperature is held to between 20° and 80° C. The suspension carrying the removed solids is drained periodically from the separator, through the lower valve 26 and this process may be automated so that it is not necessary to interrupt the process.

The existence of the separator 14 allows the original problem in the second reactor, i.e. the blocking of the outlet tubes and of the ammonia absorption column, to be corrected.

Hereafter one embodiment of the process is succinctly described.

EXAMPLE 94 kg of urea and 175 kg of cyanuric acid, recirculated from the discharge product of the second reactor, were fed per hour to the first reactor. The dwell time was about 20 minutes and the temperature of the product at the exit was 180° C. Thereafter the urea cyanurate balls were fed to the second reactor.

222 kg of cyanuric acid with an amelide content of 18% were collected at the rear end, 175 kg being recirculated to the first reactor. The gases produced were collected in the separator attached immediately at the exit of the reactor. From 200 to 500 l of suspension were purged every 12 hours from the separator, at the same time as the same volume of fresh aqueous solution were added.

What I claim is:

1. A process for preparing cyanuric acid, comprising a first step of preparation of urea cyanurate by reaction, in a first rotary reactor, of urea with recirculated cyanuric acid and a second step of pyrolysing the urea cyanurate in a second reactor, wherein said first reactor (a) is provided with a helical fin extending inwardly from the internal cylindrical surface thereof and (b) is heated to a temperature ranging from 180° to 350° C., there being obtained balls of urea cyanurate, the dryness of which facilitates the transportation thereof, at the same time as it avoids the agglomeration thereof and subsequent adherence to the walls of the second reactor, while said second reactor is rotary and is in communication, by means of a communication tube, with a solids separator vessel in which there is to be found an aqueous solution, setting a working level under which there is the access port of said tube to said vessel, said aqueous solution receiving the solid products formed in the pyrolysis and being periodically renewed by removal of the suspension formed and supply of fresh aqueous solution.

* * * * *